United States Patent [19]

De Kretser et al.

[11] Patent Number: 5,196,192
[45] Date of Patent: Mar. 23, 1993

[54] ACTIONS OF HORMONES

[75] Inventors: David M. De Kretser; David M. Robertson; mark P. Hedger, all of Victoria, Australia

[73] Assignees: Biotechnology Australia Pty. Ltd., East Roseville; Monash University, Clayton; St. Vincent's Institute of Medical Research, Fitzroy; Monash Medical Centre, Melbourne, all of Australia

[21] Appl. No.: 459,704

[22] PCT Filed: May 31, 1989

[86] PCT No.: PCT/AU89/00245

§ 371 Date: Apr. 2, 1990

§ 102(e) Date: Apr. 2, 1990

[87] PCT Pub. No.: WO89/11862

PCT Pub. Date: Dec. 14, 1989

[30] Foreign Application Priority Data

May 31, 1988 [AU] Australia ............................... P18534
Nov. 15, 1988 [AU] Australia ............................... PJ1470

[51] Int. Cl.⁵ ...................... A61K 37/04; A61K 37/02
[52] U.S. Cl. ...................................... 424/85.8; 514/8
[58] Field of Search ........................... 424/85.8; 514/8

[56] References Cited

FOREIGN PATENT DOCUMENTS

| A7101587 | 6/1987 | Australia . |
| 0210461 | 2/1987 | European Pat. Off. . |
| 0222491 | 5/1987 | European Pat. Off. . |
| 8600078 | 1/1986 | World Int. Prop. O. . |
| 8606076 | 10/1986 | World Int. Prop. O. . |
| 8805789 | 8/1988 | World Int. Prop. O. . |
| 8904668 | 6/1989 | World Int. Prop. O. . |

OTHER PUBLICATIONS

Hedger, M. P. et al., "Inhibin and Activin Regulate [³H]Thymidine Uptake by Rat Thymocytes and 3T3 Cells in Vitro", *Molecular and Cellular Endocrinology*, 61: 133-138 (1989).

European Search Report and Annex.

International Search Report and Annex.

McLachlan, R. I. et al., "The Human Placenta: A Novel Source of Inhibin", *Biochem. Biophys. Res. Comm.* 140:485-490 (1986).

Petraglia, F. et al., "Localization, Secretion, and Action of Inhibin in Human Placenta", *Science*, 237:187-189 (1987).

McLachlan, R. I., et al., "The Radioimmunoassay of Bovine and Human Follicular Fluid and Serum Inhibin", *Mol.-Cell. Endocrinol.* 46:175-185 (1986).

Eto, Y. et al., "Purification and Characterization of Erythroid Differentiation Factor (EDF) Isolated from Human Leukemia Cell Line THP-1", *Biochem. Biophys. Res. Comm.* 142:1095-1103 (1987).

Crawford, R. J. et al., "Alpha-Inhibin Gene Expression Occurs in the Ovine Adrenal Cortex, and Is Regulated by Adrenocorticotropin", *Mol. Endocrinol.* 1:699-708 (1987).

Esch, F. S. et al., "Complementary Dioxyribonucleic Acid (cDNA) Cloning and DNA Sequence Analysis on Rat Ovarian Inhibins", *Mol. Endocrinol.* 1:388-396 (1987).

Woodruff, T. K. et al., "Rat Inhibin: Molecular Cloning of Alpha-Beta-Subunit Complementary Dioxyribonucleic Acids and Expression in the Ovary", *Mol. Endocrinol.* 1:561-568 (1987).

(List continued on next page.)

Primary Examiner—Lester L. Lee
Assistant Examiner—Choon P. Koh
Attorney, Agent, or Firm—Sandler, Greenblum & Bernstein

[57] ABSTRACT

The invention relates to novel uses for inhibin, inhibin α subunit, activin inhibin or activin antagonists and compositions comprising them in the treatment or prevention of immune dysfunction and blood clotting disorders.

Methods of treatment include administration of the required agent to a host, immunization of the host with the agent or passive immunization using antibodies raised against one of these agents.

7 Claims, 8 Drawing Sheets

OTHER PUBLICATIONS

Cate, R. L. et al., "Isolation of the Bovine and Human Genes for Mu Inhibiting Substance and Expression of the Human Gene in Animal Cells", *Cell* 45:685-698.

Sporn, M. B. et al., "Some Recent Advances in the Chemistry and Biology of Transforming Growth Factor-Beta", *J. Cell Biol.* 105:1039-1045 (1987).

Kehrl, J. H. et al., "Production of Transforming Growth Factor-Beta by Human T Lymphocytes and Its Potential Role in the Regulation of T Cell Growth", *J. Exp. Med* 163:1037-1050 (1986).

Wrann, M. et al., "T Cell Suppressor Factor from Human Glioblastoma Cellsis a 12.5-kd Protein Closely Related to Transforming Growth Factor-Beta", *EMBO* 6:1633-1636 (1987).

Ueno, N. et al., "Isolated and Partial Characterization of Follistatin: A Single-Chain M 35,000 Monomeric Protein that Inhibits the Release of Follicle-Stimulating Hormone", *Proc. Natl. Acad. Sci.*, U.S.A. 84:8282-8286 (1987).

Robertson, D. M. et al., "The Isolation of Polypeptides with FSH Suppressing Activity from Bovine Follicular Fluid Which Are Structurally Different to Inhibin", *Biochem. Biophys. Res. Comm.* 149:744-749 (1987).

Morein, B. et al., "Iscom, a Novel Structure for Antigenic Presentation of Membrane Proteins from Envelop to Viruses", *Nature* 308:457-460 (1984).

McLachlan, R. I. et al., "Circulating Immunoreactive Inhibin Levels During the Normal Human Menstrual Cycle", *J. Clin. Endocrinol. Metab.* 65:954-961 (1987).

Nerenberg, S. T. et al., "Hematological Response of Response of Rabbits to Chronic, Repetitive, Severe Bleedings for the Production of Antisera", *J. Imm. Meths.* 24:19-24 (1978).

Forage, R. G. et al., "Immunization Against An Inhibin Subunit Produced by REcombinant DNA Techniques Results in Increased Ovulation Rate in Sheep", *J. Endocr.* 114:R1-R4 (1988).

Findlay, J. K. et al., "Effects of Immunization Against Recombinant Bovine Inhibin Alpha Subunit on Circulating Concentrations of Gonadotrophins in Ewes", *J. Endocrinology* 120:59-65 (1989).

ACTIONS OF HORMONES

TECHNICAL FIELD

This invention relates to secondary uses for the gonadal hormones inhibin and activin and the α subunit of inhibin and to uses for antagonists for these hormones.

BACKGROUND ART

Inhibit is a gonadal glycoprotein which preferentially suppresses FSH secretion in vitro and is believed to have a key role in the physiological control of FSH in vivo. Recently, inhibin has been isolated from bovine (Robertson et al 1985 Biochem Biophys Res Comm 126:220; Robertson et al 1986, Mol Cell Endocrinol 44:217; Fukada et al 1986 Mol Cell Endocrinol 44:55), porcine (Miyamoto et al 1985 Biochem Biophys Res Comm 129:396; Ling et al 1985, Proc Nat Acad Sci (USA) 82:7217) and ovine (Leversha et al 1987 J. Endocrinol 113:213) ovarian follicular fluids (FF). The amino acid sequence or porcine (Mason et al 1985 Nature 318:639), bovine (Forage et al 1986 Proc Nat Acad Sci (USA) 83:3091), human (Mason et al 1986 Biochem Biophys Res Comm 135:957; Steward et al 1986 FEBS 206:329), ovine (Crawford et al 1987 Mol Endocrinol 1:699; Forage et al 1987 Serono Symposium 42:89) and rat (Esch et al 1987 Mol Endocrinol 1:388; Woodruff et al 1987 Mol Endocrinol 1:561) inhibin has been determined by cloning techniques. Inhibit in a dimer of two partially homologous subunits (α and β) joined by disulphide bonds. Inhibin with two variants of the β subunit (A and B) has been isolated from porcine FF (Ling et al 1985 Proc Nat Acad Sci (USA) 82:7217) and their mRNAs also identified in the human (Mason et al 1986 Biochem Biophys Res Comm 135:957; Steward et al 1987 FEBS 206:329) and rat (Esch et al 1987 Mol Endocrinol 1:949; Woodruff et al 1987 Mol Endocrinol 1:561). Inhibin has also been isolated as two molecular weight forms (58000D and 31-32000D) which differ in the extent of processing of the α chain (Robertson et al 1986 Mol Cell Endocrinol 44:271). Bovine 58 kD inhibin is cleave to 31 kD inhibin in the presence of serum but not follicular fluid (McLachlan et al 1986 Mol Cell Endocrinol 46:175) suggesting that processing of the α subunit is extragonadal. Inhibin has also been identified as a placental product in rats and humane (McLachlan et al 1985 Biochem Biophys Res Comm 140:485; Petraglia et al 1987 Science 237:187), suggesting that it plays a role in pregnancy.

Recently, several proteins have been isolated from gonadal and other tissues and found to be structurally related to inhibin particularly to the β subunit, but with different biological activities. These proteins include activin-A and activin-AB (inhibin βAβA or βAβB subunit dimers, Vale et al 1986 Nature 321:776; Ling et al 1986 Nature 321:779) or erythroid differentiating factor (Eto et al 1987 Biochem Biophys Res Comm 142:1095); Mullerian inhibitory substance (Cate et al 1986, Cell 45:685) and transforming growth factor-β (Sporn et al 1987 J Cell Biol 105:1039). TGF-' is a potent inhibitor of lectin-induced T lymphocyte proliferation in vitro, and many patients with glioblastomas, which secrete large amounts of TGF-β, display suppressed immune functions (Kherl et al 1986 J Exp Med 163:1037; Wrann et al 1987 EMBO 6:1633).

DISCLOSURE OF THE INVENTION

Definitions

As used throughout the specification and claims "host" refers to a vertebrate host, preferably a mammalian host, and more particularly a human host.

The term "inhibin" as used throughout the specification is not restricted to inhibit isolated from a particular source and may include inhibin A $(\alpha\beta_A)$ or inhibin B $(\alpha\beta_B)$. The inhibin used may be naturally occurring or a recombinant or synthetic or semi/synthetic inhibin. It is recognised that for human applications the inhibin of choice would be a human inhibin whereas for veterinary applications one would preferably choose an inhibin derived from the appropriate animal species, unless an immune response is desired in which case an inhibin derived from a species differing from the host would be desirable. Purification and characterisation of native inhibin is described in PCT/AU85/00119. Recombinant inhibin is described in PCT/AU86/00097.

The term "activin" as used throughout the specification is not restricted to activin isolated from a particular source and may include activin A, activin AB or activin B $(\beta_B\beta_B$ dimer). The activin used may be naturally occurring or a recombinant or synthetic or semi/synthetic activin. It si recognised that for human applications the activin of choice would be a human activin derived from the appropriate animal species, unless an immune response is desired in which case an activin derived from a species differing from the host would be desirable.

The term "α subunit" as used throughout the specification and claims refers to the α subunit of inhibin including precursor forms. It is not restricted to α subunit derived from a particular source. The α subunit used may be naturally occurring or a recombinant or synthetic or semi/synthetic α subunit. It is recognised that the α subunit of choice for inducing an immune response would be derived from a species differing from the host.

The term "inhibin composition" as used throughout the specification and claims refers to a composition comprising inhibin together with a pharmaceutically acceptable carrier, diluent, excipient and/or adjuvant.

The term "α subunit composition" as used throughout the specification and claims refers to a composition comprising inhibin α subunit together with a pharmaceutically acceptable carrier, diluent, excipient and/or adjuvant.

The term "activin composition" as used throughout the specification and claims refers to a composition comprising activin together with a pharmaceutically acceptable carrier, diluent, excipient and/or adjuvant.

The term "pharmaceutically acceptable" as used through the specification and claims extends to acceptability for human use or for other vertebrate use depending on whether the host, in a particular instance, is a human or other vertebrate.

The term "inhibin antagonist" refers to antagonists acting on the α subunit, β subunit or both and includes activin, TGF-β or other molecules having an activity or effect that is opposite to that of inhibin or that blocks the action of inhibin without necessarily combining with inhibin, antibodies to inhibin or to its α subunit or other molecules that neutralise the biological activities or effects of inhibin by combining with inhibin or with the α subunit of inhibin.

The term "inhibin antagonist composition" as used throughout the specification and claims refers to a composition comprising an inhibin antagonist and/or an antagonist of the α subunit of inhibin together with a pharmaceutically acceptable carrier, diluent, excipient and/or adjuvant.

The term "activin antagonist" as used throughout the specification and claims includes molecules having an activity or effect that is opposite to that of activin or that blocks or neutralizes the action of activin without necessarily combining with activin, as well as antibodies to activin or to its subunits, inhibin, and other inhibin-like molecules such as FSP, or follistatin [Uemo et al (1987) PNAS USA 84 8282; Robertson et al (1987) Biochem Biophys Res Comm 149 744; PCT/AU88/00024].

The term "activin antagonist composition" as used throughout the specification and claims refers to a composition comprising an activin antagonists together with a pharmaceutically acceptable carrier, diluent, excipient and/or adjuvant.

The term "adjuvant" as used throughout the specification refers, in respect to immunising compositions, to an agent used to enhance the immune response of the immunised host to the immunising composition. In respect of pharmaceutical compositions which are to be administered for therapeutic or prophylactic purposes other than immunisation, the term "adjuvant" refers to an agent used to enhance the desired therapeutic or prophylactic response of the host to the composition administered.

The term "antibody composition" as used throughout the specification and claims refers to a composition comprising the appropriate antibodies together with a pharmaceutically acceptable carrier, adjuvant excipient and/or diluent.

The present invention relates to uses of the gonadal hormones inhibin and activin as well as the α subunit of inhibin and antagonists to inhibin and activin for purposes other than modulation of gonadal function.

The present invention demonstrates the bovine inhibin stimulates, while bovine activin suppresses lectin-induced proliferation of T-lymphocytes of rat thymus in vitro. Rabbits immunised with inhibin show a suppression of immunoglobulin levels compared to immunised and non-immunised control rabbits. These findings indicate that inhibin and activin are intimately involved in the regulation of immune responses. In contrast to its effects on T-lymphocytes, activin stimulates proliferation of 3T3 mouse embryo fibroblast cells in vitro but inhibin had no effect on these cells. These observations indicate that activin is a stimulatory growth factor and that the actions of inhibin and activin are cell-type specific.

Previous studies have shown that where the α subunit of inhibin is used as an immunogen, antibodies are generated that react with inhibin and neutralise its activity [Forage et al (1987) J. Endocrinol. 114 R1-R4: Findlay et al (1989) J. Endocrinology 120]. Therefore, inhibin and the α subunit of inhibin can be regarded at least as equivalent immunogens and the απsubunit may be a superior immunogen since α subunit antibodies will neutralise both inhibin A and inhibin B and no β subunit antibodies can be generated that would cross-react with activin. Based on the above findings it follows that where immunisation against inhibin is required for immunoregulatory or blood clotting purposes, immunisation against inhibin α subunit can be utilised to achieve the same end.

Based on these observations, inhibin is suitable as:
1. an immunostimulatory agent for treatment of immunosuppression states and immunodeficiency diseases, including acquired immune deficiency syndrome (AIDS) and as an agent to stimulate the immune system response to infections and tumours.
2. an immunogen for treatment of the autoimmune diseases (eg. systemic lupus erythematosus) and suppression of transplantation rejection responses. As explained above immunisation against the α subunit can also be used. It follows that other inhibin antagonists would be of use in the treatment of the autoimmune diseases and for the suppression of transplantation rejection.
3. a diagnostic for monitoring the immune status of patients. Based on these observations, activin is suitable as
1. an agent for the treatment of autoimmune diseases and for inhibition of transplantation rejection responses.
2. a growth promoter for the treatment of wounds including surgical lesions, burns, tissue grafts and chronic ulcers.

From these observations it follows that activin antagonists can be used as:
1. inhibitors of excess tissue proliferation for the treatment of conditions such as keloid.
2. immunostimulants.
3. diagnostic agents for monitoring of immune status of patients and tumor growth.

Further, the inventors have found immunisation against both inhibin and the α subunit of inhibin to effect in vivo neutralization of inhibin results in more rapid clotting of blood.

These observations indicate that inhibin acts to delay clotting and may have widespread applications to delay thrombic processes. Alternatively, antagonists to inhibin enhance the clotting process for treatment of haemorrhage and clotting disorders.

Based on these observations, inhibin is suitable as:
1. an agent for the delay of blood clotting and delays of thrombic processes.

Inhibin antagonists are suitable as:
1. agents to enhance the clotting process; and
2. agents for the treatment of haemorrhage and clotting disorders.

Inhibin or the α subunit thereof can be used as immunogens to effect more rapid blood clotting.

The invention provides a method for the treatment of immunosuppressive states or immunodeficiency diseases in a host in need of such treatment which method comprises administering an effective amount of inhibin or an inhibin composition, to said host.

Immunosuppressive states to be treated include acquired immune deficiency syndrome (AIDS).

The invention also provides a method of stimulating the immune response of a host in need of such treatment, to an infection of a tumour which method comprises administering an immunostimulatory amount of inhibin or an inhibin composition, to said host.

The invention further provides a method for the treatment of an autoimmune disease in a host in need of such treatment which method comprises immunising said host with an autoimmune disease treating amount of inhibin, the α subunit of inhibin, an α subunit composition or an inhibin composition. Alternatively, the host may be passively immunised with inhibin antibodies, α subunit antibodies, or an inhibin antibody or α subunit antibody composition. The method may comprise administering an autoimmune disease treating amount of an inhibin antagonist or inhibin antagonist composition to the host.

In another embodiment, the invention provides a method of suppressing transplantation rejection in a host in need of such treatment which method comprises immunising said host with a transplantation rejection suppressing amount of inhibin, the α subunit of inhibin or an inhibin or α subunit composition. Alternatively, the host may be passively immunised with inhibin antibodies including α subunit antibodies or with an inhibin or α subunit antibody composition. The method may comprise administering a transplantation rejection suppressing amount of an inhibin antagonists or an inhibin antagonist composition to the host.

In yet another embodiment, the invention provides a method for monitoring the immune status of a host in need of such treatment which method comprises measuring the ability of said host to respond to immunostimulation by inhibin or an inhibin composition.

The invention also provides a method for treating an autoimmune disease in a host in need of such treatment which method comprises administering to said host an autoimmune disease treating amount of activin or an activin composition.

In another embodiment, the invention provides a method of inhibiting a transplantation rejection response in a host in need of such treatment which method comprises administering a transplantation rejection suppressing amount of activin or an activin composition, to said host.

The invention also provides a method for treating a wound including a surgical lesion, burn, tissue graft or chronic ulcer in a host in need of such treatment which method comprises administering to said host a growth promoting amount of a growth promoter comprising activin or an activin composition.

The invention further provides a method of monitoring the immune status of a host in need of such treatment which method comprises measuring the levels of inhibin and/or activin in serum or tissues by radioimmunoassay or bioassay.

The invention also provides a method of monitoring tumour growth in a host in need of such treatment which method comprises measuring the levels of activin in serum or tissues by radioimmunosay or bioassay.

The invention further provides a method for inhibiting excess tissue proliferation in a host in need of such treatment which method comprises administering an effective amount of an activin antagonist or an activin antagonist composition to said host. This method would extend to immunisation against activin.

The invention still further provides a method of stimulating the immune response of a host in need of such treatment which method comprises administering an immunostimulatory amount of an activin antagonist or of an activin antagonist composition to a host in need of such treatment.

The invention provides a method of enhancing blood clotting in a host in need of such treatment which method comprises immunising said host with an immunising amount of inhibin or the α subunit of inhibin or an inhibin or α subunit composition. Alternatively, the host may be passively immunised with inhibin or α subunit antibodies or a composition comprising such antibodies.

Enhancement of blood clotting can also be achieved by administration of a blood clotting enhancing amount of at least one inhibin antagonist or an antagonist composition, to the host.

The invention also provides a method of inhibiting blood clotting in a host in need of such treatment which method comprises administration of a blood clotting inhibiting amount of inhibin or an inhibin composition to said host.

The invention includes a method of delaying thrombic processes in a host in need of such treatment, which method comprises administering a thrombic process delaying amount of inhibin or an inhibin composition to said host.

The invention also provides a method of treating haemorrhaging which method comprises administering a haemorrhaging treating amount of an inhibin antagonist or an antagonist composition to said host, including inhibin or α subunit antibodies. Haemmorrhaging could also be treated by immunising the host with inhibin, the α subunit of inhibin or with an inhibin or α subunit composition.

The invention provides vaccines for immunising hosts
1. against an autoimmune disease,
2. to suppress transplant rejection,
3. to enhance blood clotting,
4. to prevent haemorrhaging
comprising inhibin, α subunit of inhibin, an inhibin composition, or an α subunit composition.

The invention also provides a method of using inhibin in the preparation of a pharmaceutical composition for the delaying of thrombic processes.

The invention provides a method of using inhibin in the preparation of a pharmaceutical composition for the treatment of immunosuppressive states or immunodeficiency diseases.

The invention also provides a method of using inhibin in the preparation of a pharmaceutical composition for stimulating the immune response of a host to an infection or a tumour.

The invention further provides a method of using inhibin or inhibin α subunit in the preparation of an immunogen for protecting a host against an autoimmune disease.

The invention also provides a method of using an inhibin antagonist in the preparation of a pharmaceutical composition for the treatment of an autoimmune disease.

In another form, the invention provides a method of using inhibin or inhibin α subunit in the preparation of an immunogen for protecting a host against a transplantation rejection response.

The invention also provides a method of using an inhibin antagonist in the preparation of a pharmaceutical composition for the treatment of a transplantation rejection response.

In yet another form the invention provides a method of using inhibin in the preparation of a diagnostic agent for monitoring the immune status of a host.

The invention provides a method of using activin for the preparation of a pharmaceutical composition for the treatment of an autoimmune disease.

The invention also provides a method of using activin for the preparation of a pharmaceutical composition for suppressing transplant rejection.

The invention further provides a method of using activin for the preparation of pharmaceutical composition for promotion of tissue regeneration in a wound including a surgical lesion, burn, tissue graft or chronic ulcer.

In a further embodiment of the invention provides a method of using activin for the preparation of a pharmaceutical composition for monitoring the immune status of a host.

The invention provides a method of using activin for the preparation of a pharmaceutical composition for monitoring tumour grown in a host.

In another form, the invention provides a method of using an activin antagonist for the preparation of a pharmaceutical composition for inhibiting excessive tissue proliferation.

The invention also provides a method of using inhibin or the $\alpha$ subunit of inhibin for the preparation of an immunogen for enhancing blood clotting.

The invention further provides a method of using an inhibin antagonist for the preparation of a pharmaceutical composition for enhancing blood clotting.

The invention provides a method of using inhibin for the preparation of a pharmaceutical composition for inhibiting blood clotting.

The invention also provides a method of using inhibin for the preparation of a pharmaceutical composition for delaying thrombic processes.

The invention further provides a method of using inhibin or the $\alpha$ subunit thereof for the preparation of an immunogen for preventing haemorrhaging.

The invention also provides a method of using an inhibin antagonist for the preparation of a pharmaceutical composition for the treatment of haemorrhaging.

For those methods of the invention which comprise passive immunisation the invention provides inhibin antibodies, $\alpha$ subunit antibodies or compositions comprising inhibin or $\alpha$ subunit antibodies to be used as passive vaccines.

The amount of inhibin, activin, inhibin $\alpha$ subunit, inhibin antagonist or activin antagonist that may be combined with carrier to produce a single dosage form will vary depending upon the host to be treated and the particular mode of administration.

It will be understood, also, that the specific dose level for any particular patient will depend upon a variety of factors including the activity of the specific compound employed, the age, body weight, general health, sec, diet, time of administration, route of administration, rate of excretion, drug combination, the particular immunoregulatory or blood clotting state being treated and the severity of the particular condition undergoing treatment.

The compositions of the present invention may be administered orally, parenterally, by inhalation spray, rectally, vaginally or topically in dosage unit formulations containing conventional, non-toxic, pharmaceutically acceptable carriers, diluents, adjuvants and/or excipients as desired.

The term parenteral as used herein includes subcutaneous injections, intravenous, or intramuscular injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The term "pharmaceutically acceptable adjuvant" can mean either the standard compositions which are suitable for human administration or the typical adjuvants employed in animal vaccinations.

Suitable adjuvants for the vaccination of animals and humans include but are not limited to oil emulsions such as Freud's complete or incomplete adjuvant (not suitable for human or livestock use), Marcol 52: Montanide 888 (Marcol is a Trademark of Esso. Montanide is a Trademark of SEPIC, Paris), squalane or squalene, Adjuvant 65 (containing peanut oil, mannide mooleate and aluminum monostearate), mineral gels such as aluminum hydroxide, aluminum phosphate, calcium phosphate and alum, surfactants such as hexadecylamine, octadecylamine, lysolecithin, dimethyldioctadecylammonium bromide, N,N-dioctadecyl-N',N'-bis(2-hydroxyethyl)propanediamine, methoxyhexadecylglycerol and pluronic polyols, polyanions such as pyran, dextran sulfate, polyIC, polyacrylic acid and carbopol, peptides and amino acids such as muramyl dipeptide, dimethylglycine, tuftsin and trehalose dimycolate. The active substances of the present invention can also be administered following incorporation into liposomes or other micro-carriers, or after conjugation to polysaccharides, proteins or polymers or in combination with Quil-A to form "Iscoms" (immunostimulating complexes) (Morein et al., Nature 308, 457-460 [1984]). Other adjuvants suitable for use in the present invention include fusion proteins or conjugates comprising the active compound of interest together with an integral membrane protein of prokaryotic or eukaryotic origin, such as TraT.

Routs of administration, dosages to be administered as well as frequency of injections are all factors which can be optimized using ordinary skill in the art. Typically, the initial vaccination is followed some weeks later by one or more "boosters" vaccinations, the net effect of which is the production of high titres of antibodies against the immunogen.

Suppositories for rectal or vaginal administration of the compositions of the invention can be prepared by mixing the composition with a suitable nonirritating excipient such as cocoa butter, theobroma oil, glycerinated gelatin or polyethylene glycols which are solid at ordinary temperatures but liquid at the rectal or vaginal temperature or by contact with fluids present in the appropriate cavity and will therefore melt in the rectum or vagina and release the drug.

Compositions for topical administration include creams, ointments and pastes. The ingredients that constitute the base of ointments (e.g. petrolatum, waxes) are melted together; powdered drug components are added ant the mass stirred with cooling. Generally, the product is then passed through a roller mill to achieve the particle-size range desired for the dispersed solid. Pastes are ointments with relatively large, dispersed solid content, and are prepared similarly.

Creams are semisolid emulsions, either water-in-oil or oil-in-water. A solid ingredient can be added to the appropriate phase before emulsification or may be dispersed at some point after the emulsification step. Topical dosage forms include disc dosage form systems that have been used for the transdermal delivery of therapeutic agents. They provide uniform and prolonged drug release.

Solid dosage forms for oral administration may include capsules, tablets, pills, powders, and granules. In such solid dosage forms, inhibin activin, α subunit or antagonists may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include nanoparticles, microcapsules, LTB conjugates, cholera or its B subunit as a conjugate, or vitamin B12 conjugates in pharmaceutically acceptable emulsions, syrups, solutions, suspensions, and elixirs containing inert diluents commonly used in the art, such as water. Such compositions may also comprise adjuvants, such as wetting agents, emulsifying and suspending agents or TraT as a conjugate, and sweetening, flavoring, and perfuming agents including sugars such as sucrose, sorbitol, fructose etc, glycols such as polyethylene glycol, propylene glycol etc, oils such as sesame oil, olive oil, soybeam oil etc, antiseptics such as alkylparahydroxybenzoate etc, and flavour such as stawberry flavour, peppermint etc.

An advantage of the therapeutic methods disclosed herein is that the agents to be used are natural products which have been shown to play a physiological role.

Such an approach is of use in avoiding cytotoxicity problems experienced with available drugs.

BEST MODE AND OTHER MODE(S) FOR CARRYING OUT THE INVENTION

Figure 1:
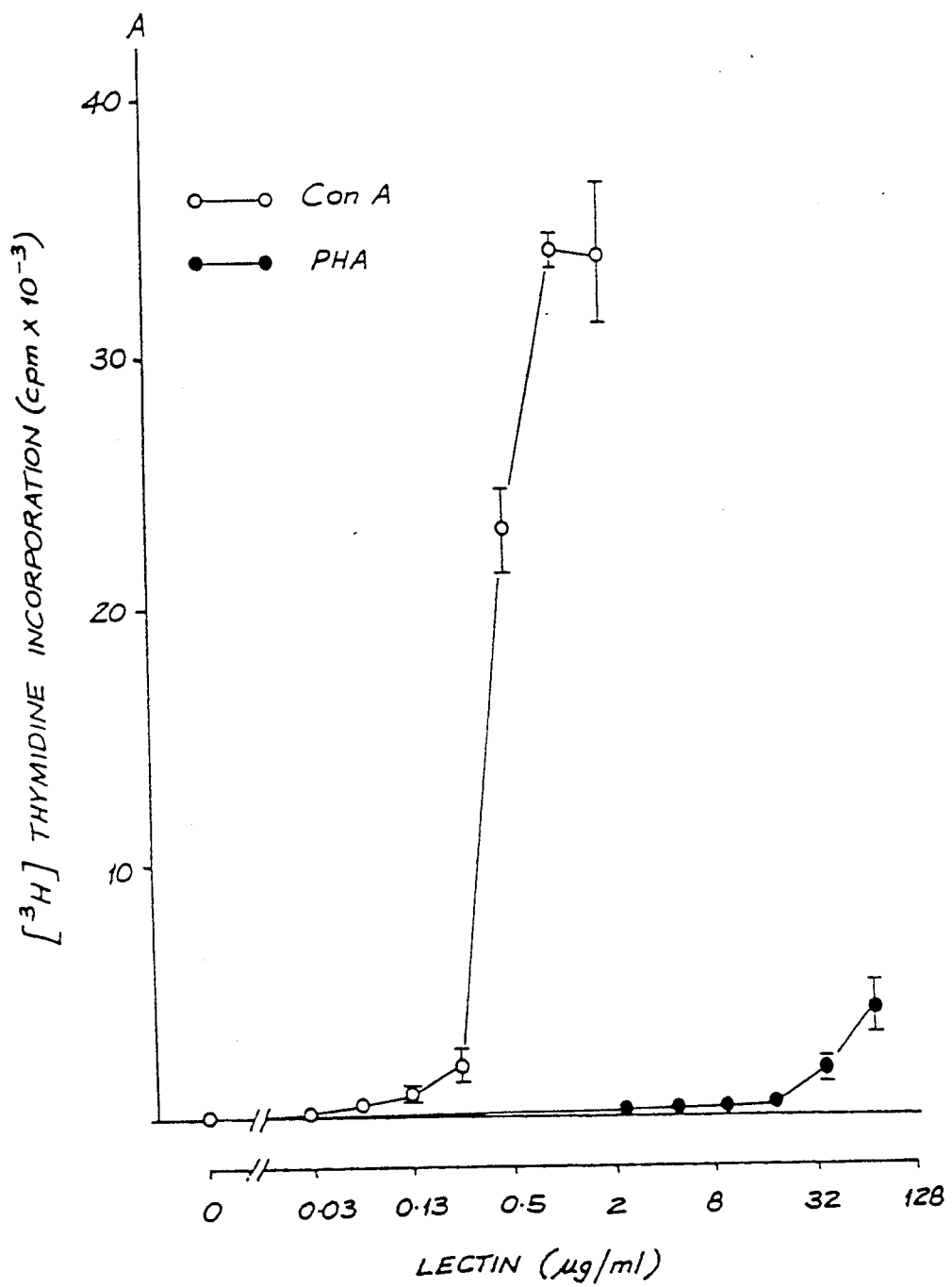
FIG. 1A shows the stimulation of tritiated thymidine incorporation into rat T-lymphocytes in vitro by the non-specific mitogens Concanavalin A (Con A) and phytohaemagglutinin (PHA). Values are mean±SEM (n=4 replicates).
FIG. 1B shows the stimulation of tritiated thymidine incorporation into rat T-lymphocytes by bovine 31 kD inhibin in the absence and presence of submaximal doses of Con A (0.125 µg/ml) or PHA (50 µg/ml). There was no effect of inhibin in the presence of maximally stimulating dose (1 µg/ml) of Con A. Values are mean±SEM (n=4 replicates).

In the method for the treatment of immunosuppressive states or immunodeficiency diseases, an effective amount of inhibin or an inhibin composition is administered to the host.

The inhibin composition for this purpose is prepared by mixing, preferably homogenously mixing, inhibin with a pharmaceutically acceptable carrier, diluent, excipient and/or adjuvant using standard methods of pharmaceutical preparation.

The amount of inhibin required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the immunosuppressive state or immunodeficiency disease undergoing treatment.

Inhibin or inhibin compositions for use in the treatment of immunosuppressive states or immunodeficiency diseases include those to be administered orally, parenterally, by inhalation spray, rectally, vaginally or topically in unit dosage formulations containing conventional, non-toxic, pharmaceutically acceptable carriers, diluents, excipients and/or adjuvants as desired.

In the method for stimulating the immune response of a host to an infection or to a tumour, an immune response stimulating amount of inhibin or an inhibin composition is administered to the host.

The inhibin composition for this purpose is prepared by mixing, preferably homogeneously mixing, inhibin with a pharmaceutically acceptable carrier, diluent, excipient and/or adjuvant using standard methods of pharmaceutical preparation.

The amount of inhibin required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the infection or tumour undergoing treatment.

Inhibin or inhibin compositions for use in the stimulation of an immune response to an infection or tumour include those to be administered orally, parenterally, by inhalation spray, rectally, vaginally or topically in unit dosage formulations containing conventional, non-toxic, pharmaceutically acceptable carriers, diluents, excipients and/or adjuvants as desired.

In the method for treatment of autoimmune disease, the host is immunised with an autoimmune disease treating amount of inhibin or an inhibin composition, α subunit or a α subunit composition. Immunisation may also be passive immunisation with the host receiving inhibin antibodies or an antibody preparation comprising antibodies raised against inhibin or the α subunits of inhibin. The antibodies are raised by immunising a host capable of raising an immune response to inhibin with inhibin, α subunit, or an inhibin or α subunit composition, and administered either as antibodies or as an antibody composition. Alternatively, an autoimmune disease treating amount of activin or an activin composition or other inhibin antagonist or other inhibin antagonist composition is administered to the host.

The inhibin composition, activin composition, α subunit composition, inhibin antagonist composition or antibody composition for this purpose is prepared by mixing, preferably homogenously mixing, inhibin, activin, α subunit, inhibin antagonist or inhibin or α subunit antibodies respectively with a pharmaceutically acceptable carrier, diluent, excipient and/or adjuvant using standard methods of pharmaceutical preparation.

The amount of inhibin, α subunit, inhibin antagonist, activin, or inhibin or α subunit antibodies required to produce a single dosage form will vary depending upon the host to be treated and the particular mode of administration. The specific dose level for any particular patient will depend upon a variety of factors including the activity of the specific molecule employed, the age, body weight, general health, sex, and diet of the patient, time of administration, route of administration, rate of excretion, drug combination and the severity of the autoimmune disease undergoing treatment.

Inhibin, α subunit, inhibin or α subunit compositions, activin, activin compositions, inhibin antagonist or inhibin antagonist compositions for use in the treatment of autoimmune diseases include those to be administered orally, parenterally, by inhalation spray, rectally, vaginally or topically in unit dosage formulations containing conventional, non-toxic, pharmaceutically acceptable carriers, diluents, excipients and/or adjuvants as desired. Antibodies or antibody compositions are administered parenterally. In newborns they may also be administered orally.

In the method of suppressing transplantation rejection the host is immunised with a transplantation rejection suppressing amount of inhibin, and inhibin composition, α subunits or an α subunit composition. Immunisation may also be passive immunisation with the host receiving an antibody preparation comprising antibodies raised against inhibin or inhibin α subunit. The antibodies are raised by immunising a host capable of raising an immune response to inhibin with inhibin or an inhibin composition or α subunit or an α subunit composition, and administered either as antibodies or as an antibody composition. Alternatively, transplantation rejection may be suppressed by administered a transplantation rejection suppressing amount of activin or an activin composition or an inhibin antagonist or an inhibin antagonist composition to the host.

The inhibin, α subunit, activin, inhibin antagonist or antibody composition for this purpose is prepared by mixing, preferably homogenously mixing, inhibin, α subunit, activin, inhibin antagonist or antibodies respectively with a pharmaceutically acceptable carrier, diluent, excipient and/or adjuvant using standard methods of pharmaceutical preparation.

The amount of inhibin, α subunit, activin, inhibin antagonist or antibody required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the transplantation rejection undergoing treatment.

Inhibin, α subunit or inhibin or α subunit compositions or inhibin antagonist or inhibin antagonist compositions or activin or activin compositions for use in the suppression of transplantation rejection include those to be administered orally, parenterally, by inhalation spray, rectally, vaginally, or topically in unit dosage formulations containing conventional, non-toxic, pharmaceutically acceptable carriers, diluents, excipients and/or adjuvants as desired. Inhibin antibodies, α subunit antibodies, or inhibin antibody compositions or α subunit antibody compositions are administered parenterally. In newborns they may also be administered orally.

In the method for monitoring the immune status of a host, the patient is treated with an immunostimulatory dose of inhibin and subsequently monitored for the ability to respond to changes in immune system parameters, particularly lymphocyte numbers and immunoglobulin levels in the circulating blood. A poor response would be indicative of imunodeficiency. Serum or biopsy tissue from organs of the immune system of a patient are collected and assayed for inhibin or activin levels by radioimmunoassay or bioassay. Low levels of inhibin or high levels of activin would indicate immunodeficiency.

In the method for inhibiting excessive tissue proliferation an effective amount of an activin antagonist or an activin antagonist composition is administered to the host.

The activin antagonist composition for this purpose is prepared by mixing, preferably homogenously mixing, an activin antagonist with a pharmaceutically acceptable carrier, diluent, excipient and/or adjuvant using standard methods of pharmaceutical preparation.

The amount of activin antagonist required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the excessive tissue proliferation undergoing treatment.

Activin antagonists or activin antagonist compositions for use in the inhibition of excessive tissue proliferation include those to be administered orally, parenterally, by inhalation spray, rectally, vaginally, or topically in unit dosage formulations containing conventional, non-toxic, pharmaceutically acceptable carriers, diluents, excipients and/or adjuvants as desired.

In the method for promoting tissue regeneration in a wound including a surgical lesion, burn, tissue graft or chronic ulcer, a tissue regeneration promoting amount of activin or an activin composition is administered to the host.

The activin composition for this purpose is prepared by mixing, preferably homogenously mixing, activin with a pharmaceutically acceptable carrier, diluent, excipient and/or adjuvant using standard methods of pharmaceutical preparation.

The amount of activin required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the wound, burn, tissue graft or chronic ulcer undergoing treatment.

Activin or activin compositions for use in the promotion of tissue regeneration include those to be administered orally, parenterally, by inhalation spray, rectally, vaginally, or topically in unit dosage formulations containing conventional, non-toxic, pharmaceutically acceptable carriers, diluents, excipients and/or adjuvants as desired.

In the method for monitoring tumour growth serum or tumour biopsy tissue is collected from a patient and assayed for activin levels by radioimmunoassay or bioassay. High levels would be indicative of tumour growth.

In the method for enhancing blood clotting, the host is immunised with inhibin, the α subunit of inhibin or an inhibin or α subunit composition. Immunisation may also be passive immunisation with the host receiving an antibody preparation comprising antibodies raised against inhibin or α subunit. The antibodies are raised by immunising an host capable of raising an immune response to inhibin, α subunit or an inhibin or α subunit composition, and administered either as antibodies or as an antibody composition. Alternatively, a blood clot enhancing amount of an inhibin antagonist or an inhibin antagonist composition is administered to the host.

The inhibin, α subunit, inhibin antagonist or antibody composition for this purpose is prepared by mixing, preferably homogenously mixing, inhibin, α subunit or an inhibin antagonist or inhibin or α subunit antibodies respectively with a pharmaceutically acceptable carrier, diluent, excipient and/or adjuvant using standard methods of pharmaceutical preparation.

The amount of inhibin, α subunit, inhibin antagonist, or antibodies required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the clotting condition undergoing treatment.

The inhibin, α subunit, antibody or antagonist composition for use in the enhancement of blood clotting include those to be administered orally, parenterally, by inhalation spray, rectally, vaginally, or topically in unit dosage formulations containing conventional, non-toxic, pharmaceutically acceptable carriers, diluents, excipients and/or adjuvants as desired. Antibodies or antibody compositions are administered parenterally. In newborns they may also be administered orally.

In the method for inhibiting blood clotting, inhibin, or an inhibin composition is administered to the host.

The inhibin composition for this purpose is prepared by mixing, preferably homogenously mixing, inhibin or α subunit respectively with a pharmaceutically acceptable carrier, diluent, excipient and/or adjuvant using standard methods of pharmaceutical preparation.

The amount of inhibin required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the clotting condition undergoing treatment.

The inhibin compositions for use in the inhibition of blood clotting include those to be administered orally, parenterally, by inhalation spray, rectally, vaginally, or topically in unit dosage formulations containing conventional, non-toxic, pharmaceutically acceptable carriers, diluents, excipients and/or adjuvants as desired.

In the method for delaying thrombic processes, inhibins, or an inhibin composition is administered to the host.

The inhibin composition for this purpose is prepared by mixing, preferably homogeneously mixing, inhibin or α subunit respectively with a pharmaceutically acceptable carrier, diluent, excipient and/or adjuvant using standard methods of pharmaceutical preparation.

The amount of inhibin required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the thrombic condition undergoing treatment.

The inhibin compositions for use in the delay of thrombic processes include those to be administered orally, parenterally, by inhalation spray, rectally, vaginally, or topically in unit dosage formulations containing conventional, non-toxic, pharmaceutically acceptable carriers, diluents, excipients and/or adjuvants as desired.

In the method for treatment for haemorrhaging an antagonist of inhibin or an inhibin antagonist composition is administered to the host. Alternatively the host may b immunised with inhibin or the α subunit of inhibin or an inhibin or α subunit composition or passively immunised with inhibin or α subunit antibodies or compositions comprising inhibin or α subunit antibodies.

The inhibin antagonist, inhibin, α subunit or antibody compositions for this purpose are prepared by mixing, preferably homogenously mixing, and inhibin antagonist, inhibin, α subunit, or antibodies respectively with a pharmaceutically acceptable carrier, diluent, excipient and/or adjuvant using standard methods of pharmaceutical preparation.

The amount of inhibin antagonist, inhibin, α subunit, or antibody required to produce a single dosage form will vary depending upon the host to be treated and the particular mode of administration. The specific dose level for any particular patient will depend upon a variety of factors including the activity of the specific inhibin employed, the age, body weight, general health, sex, and diet of the patient, time of administration, route of administration, rate of excretion, drug combination and the severity of the haemorrhaging to be treated.

The antagonist composition for use in the treatment of haemorrhaging include those to be administered orally, parenterally, by inhalation spray, rectally, vaginally, or topically in unit dosage formulations containing conventional, non-toxic, pharmaceutically acceptable carriers, diluents, excipients and/or adjuvants as desired. Inhibin antibodies, α subunit antibodies, or inhibin antibody compositions or α subunit antibody compositions are administered parenterally. In newborns they may also be administered orally.

EXAMPLE 1

Effect of inhibin and activin on the proliferation of rat T-lymphocytes in vitro A conventional T-lymphocyte proliferation assay was employed as follows;

Thymuses from 60-70 d Sprague-Dawley male rats were exercised under sterile conditions, the capsule cut and T-lymphocytes recovered mainly from the cortical region by manipulation of the tissue with blunt probes. The cells were washed in Dulbecco's Modified Eagle's Medium (DMEM) and plated (0.8 million cells/well) in 96 well tissue culture plates in the presence of test substances in a final volume of 250 μl DMEM containing 5% fetal calf serum (FCS). Cells were incubated at 37° C. for 72 hr at which time tritiated thymidine (50 μl, 0.5 μCi/well, 6.7 Ci/mmol) was added and the cells incubated a further 16-20 hrs at 37° C.

The media containing the cells were collected, the cells washed with 10 mM phosphate pH7-buffered 0.9% NaCl. 10% trichloroacetic acid (TCA, 1 ml) was added and the precipitate collected by centrifugation. The precipitate was washed with 10% TCA (1 ml) followed by methanol (1 ml). The resulting precipitate was dissolved in 0.3 M NaOH (100 μl) for 10 min at room temperature. 0.3 M hydrochloric acid (100 μl) was added and the sample counted by liquid scintillation in a γ counter.

Inhibin and activin were purified from bovine follicular fluid by precedures already described (Robertson et al 1985 Biochem Biophys Res Comm 126:220, Robertson et al 1986 Mol Cell Endocrinol 44:271; McLachlan et al 1987 J Clin Endocrinol Metab 65:954).

The results in FIG. 1 show that in the absence of Con A and PHA or in the presence of a submaximal dose of Con A (0.125 μg/ml), inhibin showed a small but significant (p<0.05) stimulation of thymidine incorporation by T-lymphocytes only at the highest dose employed (5 mM). However, in the presence of 50 μg/ml PHA, inhibin stimulated (p<0.001) thymidine uptake at all doses above 0.5 mM with a plateau of stimulation observed at 2.5 nM (ED50 0.7 nM). Inhibin had no detectable effect on T lymphocytes maximally stimulated by Con A.

Figure 2:
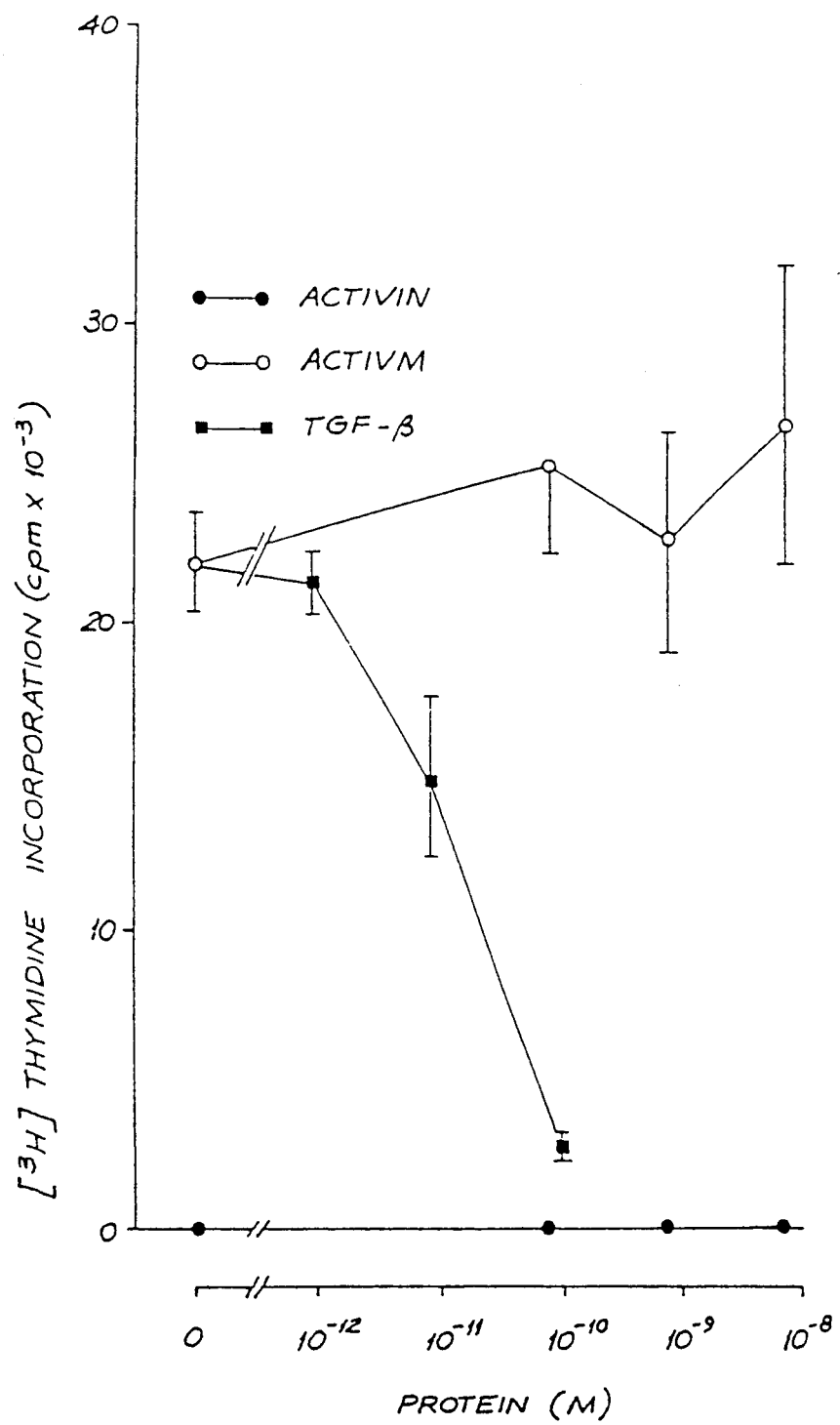
FIG. 2 shows the suppression by porcine TGF-β of tritiated thymidine incorporation into rat T-lymphocytes in the absence and presence of a maximal dose of Con A (1 µg/ml). Values are mean±SEM (n=45 replicates). *p<0.05 compared with control.
Figure 3:
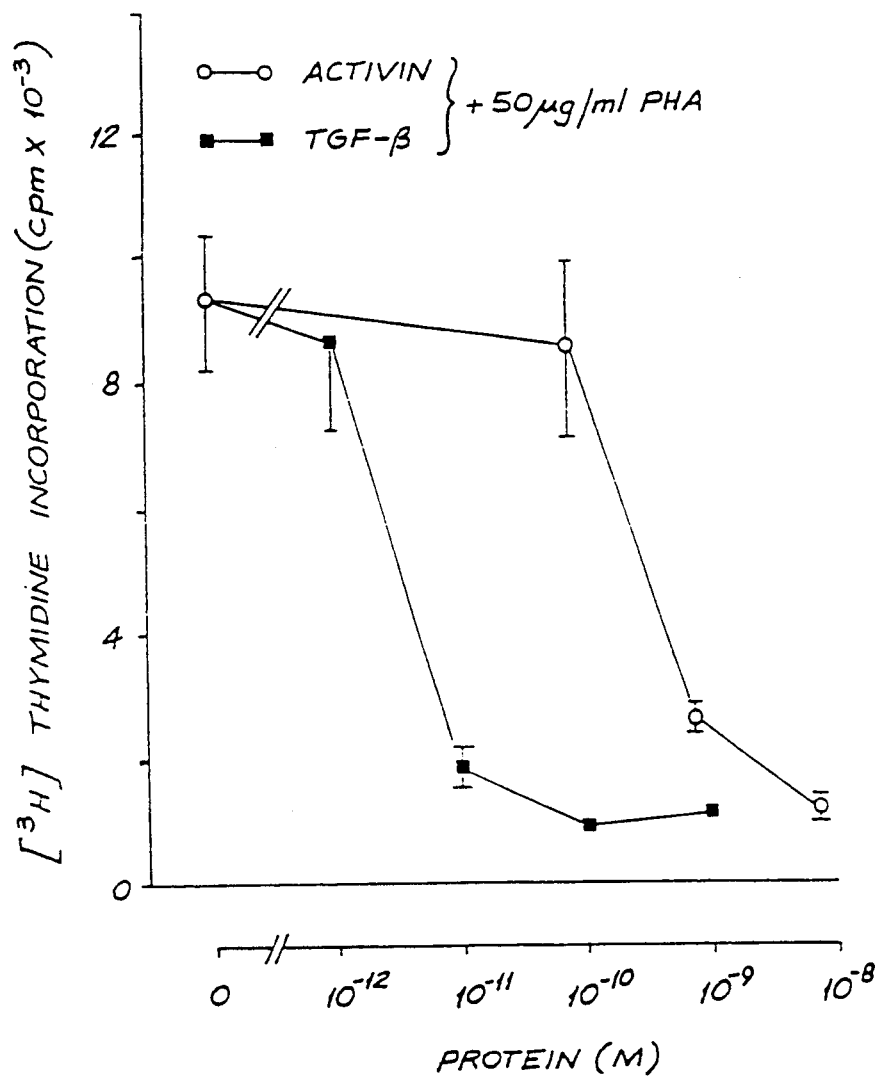
FIG. 3 shows inhibition of tritated thymidine incorporation into rat T-lymphocytes by bovine activin and TGF-β in the presence of an submaximal dose of PHA (50 µg/ml).

TGF-β inhibited uptake by lymphocytes maximally-stimulated by Con A, with an ID50 of 0.,02 nM (FIG. 2). Although bovine activin showed no effect in this experiment, other studies (data not shown) showed that the highest dose of activin (10 nM) can suppress maximally stimulated lymphocytes indicating a variable effect of activin at high doses. There was no effect of activin up to 10 nM on unstimulated lymphocytes. Both TGF-β and activin inhibited PHA-stimulated (50 μg/ml) thymidine uptake by T lymphocytes, with ID50 values of 0.005 nM and 0.4 nM, respectively (FIG. 3).

EXAMPLE 2

The effect of inhibin and activin on the proliferation of a mouse 3T3 fibroblastic cell line Mouse Balb/c 3T3 embryo fibroblasts were maintained at 37° C. in DMEM supplemented with glucose (4.5 g/l) and 10% FCS. Monolayers of these cells were trypsinised and the released cells were suspended in DMEM containing 10% FCS at a concentration of 50,000/ml. Samples of 200 μl were placed into 96 well culture plates and incubated for 4 days. The medium was replaced with DMEM containing 0.5% FCS. Cells were then incubated at 37° C. for 20 hr at which time tritiated thymidine (10 μl, 0.4 μCi/well, 6.7 Ci/mmole) was added and the cells incubated a further 2 hrs at 37° C. The cells were washed with distilled water, 5% trichloroacetic acid (TCA, 0.2 ml) added and the precipitate was washed with 10% TCA. The precipitate was dissolved in 0.3 M NaOH (100 μl) for 10 min at room temperature. Hydrochloric acid (100 μl, 0.3 M) was added and the sample counted by liquid scintillation n a γ counter.

Figure 4:
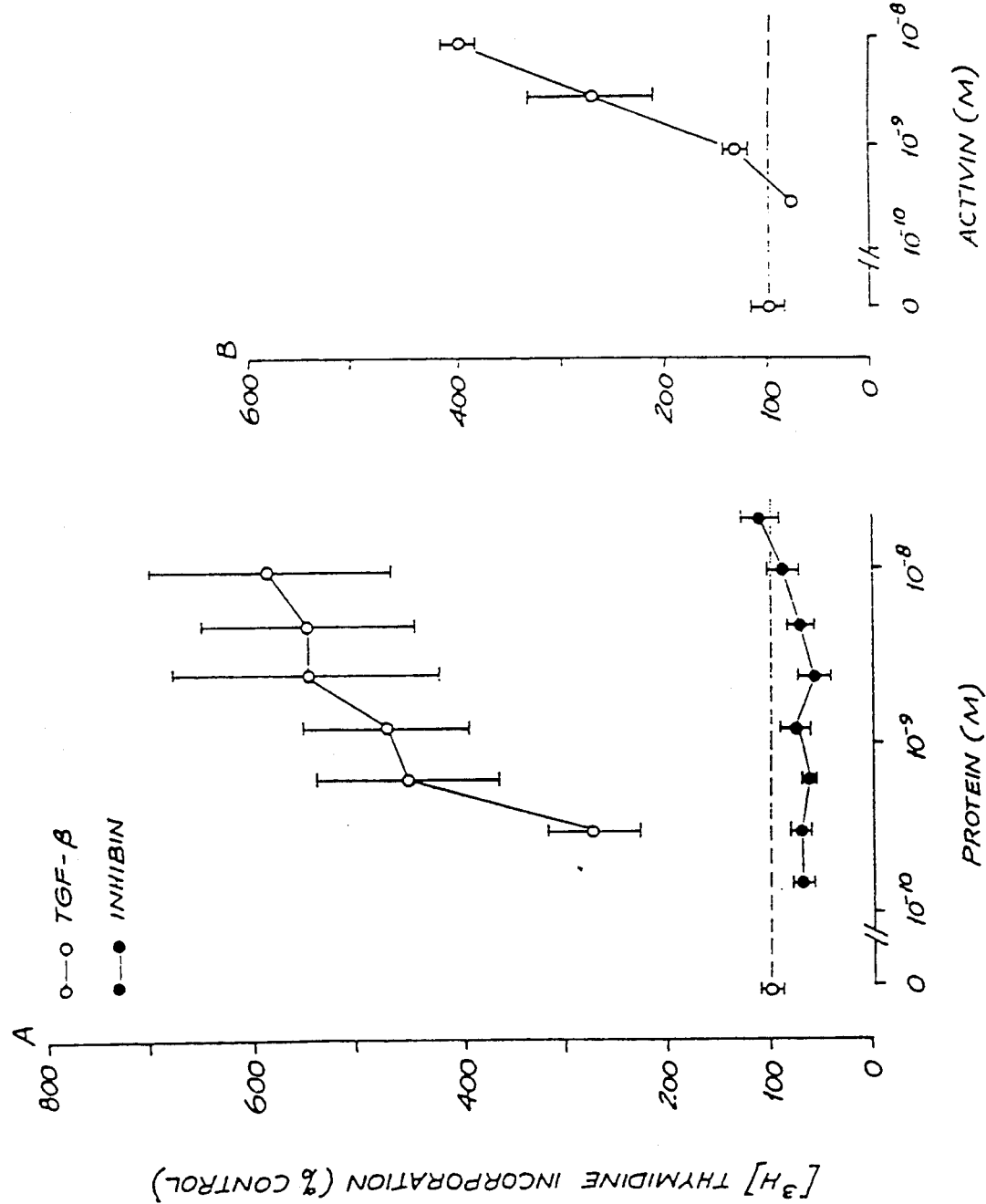
FIG. 4 shows stimulation by bovine activin and porcine TGF-β of tritiated thymidine incorporation into mouse 3T3 cells in vitro. Bovine inhibin had no effect in this system. Values are mean±SEM (n=4 replicates).

In contrast to the responses observed for T-lymphocytes in vitro, inhibin did not stimulate the proliferation of 3T3 cells, up to a maximum dose of 30 nM (FIG. 4). However, activin stimulated 3T3 cell proliferation at doses above 3 nM, but TGF-β stimulated proliferation even at the lowest dose employed (0.3 nM).

EXAMPLE 3

IgG Levels in sera from inhibin-immunised and control rabbits

Since inhibin is a natural stimulator of the immune system, removal or neutralisation of inhibin by direct immunisation could result in lower serum 1 gG levels due to the neutralisation per se and to inhibitory effects of the remaining activin and/or TGF-β. To test this intact New Zealand male rabbits were used. Sera from a pool of normal rabbits and serum from a rabbit immunised against bovine 31 kD inhibin were collected separately and immunoglobulin (IgG) fraction isolated following an initial 45% ammonium sulphate precipitation step and a fractionation step of Protein A immobolised to Sephacryl S200.

From 20 ml serum, 38.2 mg IgG was recovered from control animals compared with 23.4 mg from the immunised animal. Details of the immunisation procedure and characterization of this antiserum have been previously described (McLachlan et al 1986 Mol Cel, Endocrinol 46:175).

Figure 5A:
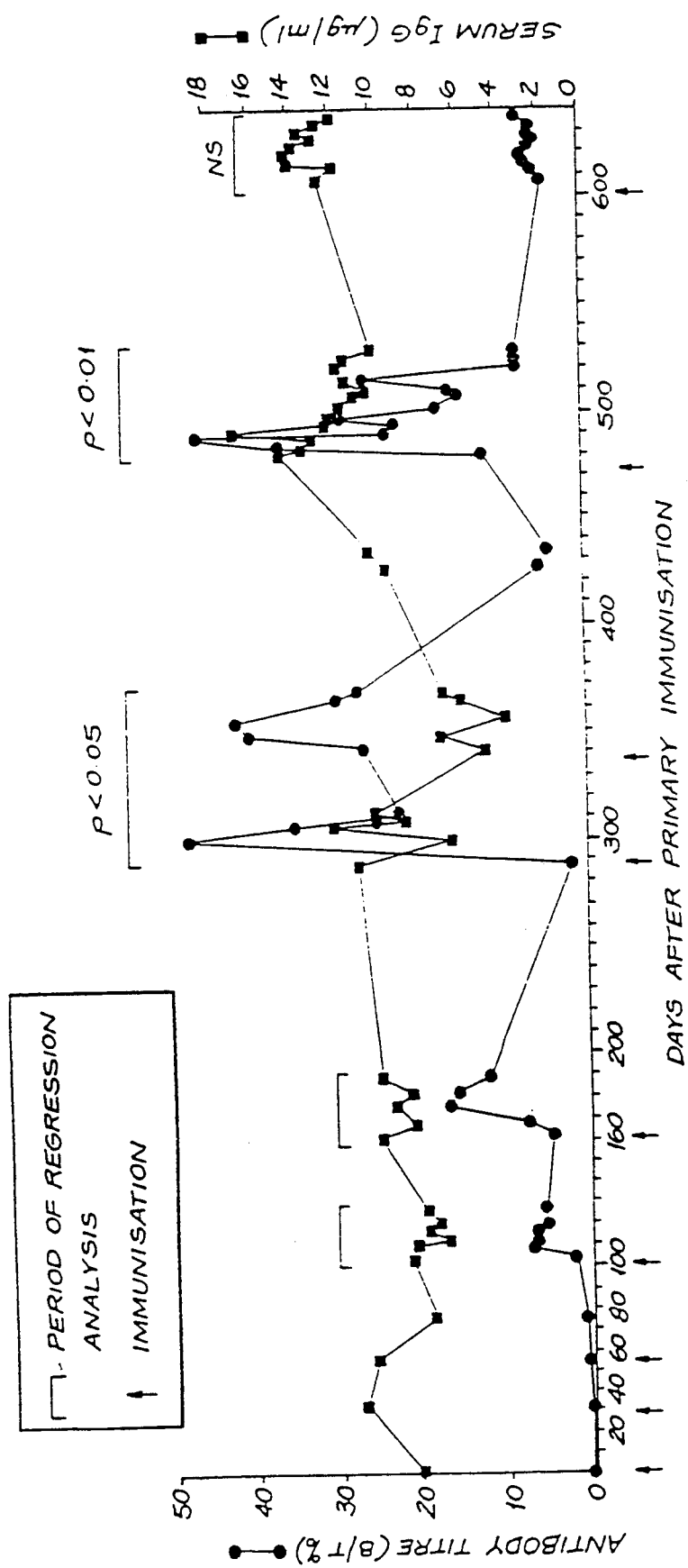
FIG. 5 shows profiles of serum IgG levels and inhibin-specific or control protein-specific antibody titre in rabbits receiving multiple immunisations with bovine inhibin (FIG. 5A) and control protein (FIG. 5B). NS: regression is not significant.
Figure 5B:
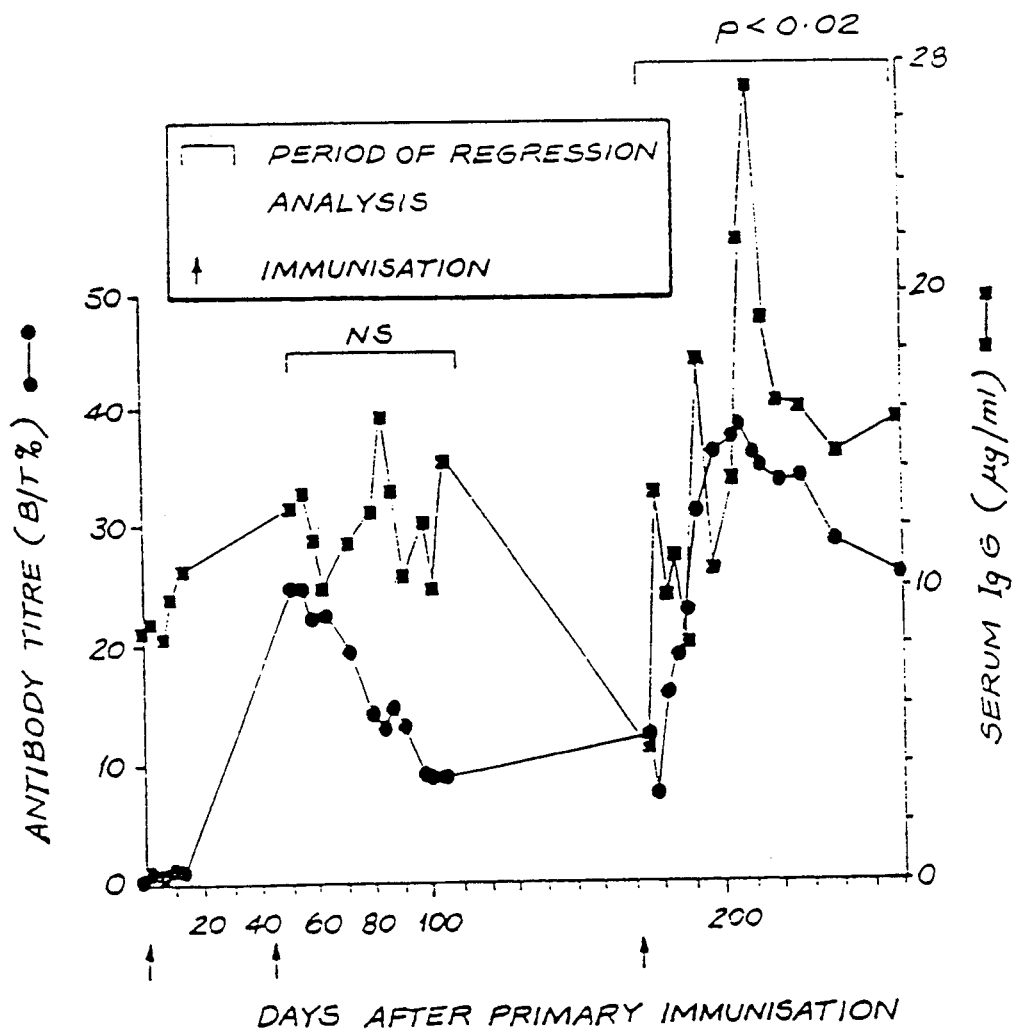

In further studies, serum IgG levels were determined by sandwich enzyme-linked immunosorbent assay. In this assay, the solid phase was coated with sheep anti-rabbit IgG and incubated with either rabbit IgG standard or rabbit sera unknowns as multiple dilutions. The level of bound IgG in the standard or sample was detected with peroxidase-labelled goat anti-rabbit IgG. Serum IgG levels were determined in 3 rabbits receiving multiple immunisations with bovine 58 or 31 kD inhibin and two rabbits receiving multiple injections with another protein structurally unrelated to inhibin and showing no effect on thymocyte proliferation (control protein). The antibody titre was assessed from binding of the respective iodinated protein to serum at a final dilution of 1:6000. Examples of the changes in serum IgG and inhibin antibody titre following immunisation with inhibin or control protein is shown in FIG. 5.

In order to analyse this relationship, the change in serum IgG levels after each secondary immunisation was determined from the significance of the regression of the IgG levels during the periods when the antibody titre was above 5 and 10% binding, respectively. As seen in Table 1, in the inhibin-immunised rabbits, 3 of 9 immunisations which resulted in antibody titres >10% showed a significant decrease in serum IgG, the remainder showing no change. In contrast, in control animals two immunisations caused an increase in IgG levels while two showed no change. It is concluded that inhibin immunisation can cause a suppression in serum IgG levels.

The results of Examples 1-3 indicate that inhibin stimulates the immune system at physiological doses, at least in part by direct stimulation of lymphocyte function as well as by enhancing the response of lymphocytes to mitogenic, and presumably antigenic, stimulation. In accordance with these observations in vitro, blocking endogenous inhibin action in vivo by passive immunisation results in a reduced capacity for immunoglobulin production. The immunostimulatory actions of inhibin is specific, as inhibin had no effect on the proliferation of 3T3 cells in vitro.

In contrast to the effects of inhibin, activin suppresses lymphocyte function at physiological doses, although at higher doses than observed with TGF-$\beta$. Interestingly, the action of activin on 3T3 cell proliferation in vitro was opposite to its effects on the lymphocytes, being stimulatory at physiological doses. It is also postulated that inhibin and activin are also involved in regulating the unique immunologically privileged environments of the gonads and pregnant uterus, as well as growth regulation. Consequently, inhibin and activin have applications as therapeutic and diagnostic agents in a broad range of clinical conditions related to immune dysfunction and tissue growth promotion.

TABLE 1

Changes in IgG levels after booster immunisation with bovin inhibin or control protein

| Immunogen | Titre | No. of immunisations resulting in a change or no change in serum IgG levels. | | | |
|---|---|---|---|---|---|
| | | Increase | No Change | Decrease | Total |
| Inhibin | <5% | 1 | 0 | 0 | 1 |
| | 5-10% | 0 | 3 | 0 | 3 |
| | >10% | 0 | 6 | 3 | 9 |
| Control | <10% | 0 | 0 | 0 | 0 |
| Proetin | >10% | 2 | 2 | 0 | 4 |

For methodological details see text.

EXAMPLE 4

Effects of Inhibin Immunisation on Clotting Time in Adult Male Castrate Rabbits

Two male adult castrate New Zealand rabbits, aged approximately 2 years (#749 and #1989) were immunised with purified bovine 31 kD inhibin (10-20 $\mu$g hormone/1.5-6 ml of Dulbecco's Phosphate buffer pH 7.0 (40%+Montanide 888: Marcol 52 1:9 (60%)). Following an initial injection and 3-7 boosters the clotting time of the blood collected via the marginal ear vein using the flask suction method (Nerenberg et al, J. Imm Meths 24 1978, 19-24) was determined (see Table 2).

TABLE 2

| Treatment | Rabbit Number | Clotting time (seconds)* |
|---|---|---|
| Immunised | 749 & 1989 | 15-60 |
| Controls | 1 & 2 | 120-480 |

*Observations were made by two independent operators on several occasions.

EXAMPLE 5

Tracer Binding Assay

Sheep sera were diluted 1:500 in 0.01 M phosphate buffered saline (36 g NaCl, 5.52 g Na $H_2PO_4 2H_2O$, 0.4 g Na Azide in 4 liters of distilled water at pH 7.4, containing 0.5% bovine serum albumin [BSA] referred to as buffer, below) and 100 $\mu$l of this was added to a plastic tube; 200 $\mu$l of buffer was also added. To this was added 100 $\mu$l of approximately 10,000 cpm of $^{125}$I-31 kD purified bovine inhibin. The tubes were incubated overnight at room temperature (14°-20° C.). A second antibody (anti-sheep IgG raised in donkey) was added, diluted 1:20 with buffer, and added 100 $\mu$l to each tube then incubated for 30-45 min followed by the addition of 1 ml of 6% polyethylene Glycol 6000 (PEG). Tubes were vortexed and centrifuged for 30 min at 2,500 rpm. The supernatants were decanted and allowed to drain. Pellets were counted in a multi-channel $\gamma$-counter and results expressed as a % of total radioactive counts added (minus NSB) giving % binding of 31 kD bovine inhibin to the antibodies in the sera.

EXAMPLE 6

Effects of Recombinant Inhibin $\alpha$ subunit Immunisation on Clotting Time in Adult intact Female Sheep Nine ewes were immunised with bovine inhibin $\alpha$ subunit fused to part of $\beta$-galactosidase (30 $\mu$g protein/ml of saline+Montanide 888: Marcol 52 1:9 (50:50)). Animals were given a primary and booster immunisations (intramuscularly, i.m.) 4 weeks apart and left for several months. Blood (10 ml) was collected by vacutainer and the clotting time assessed using a stopwatch. Inhibin antibody titres were determined by tracer binding assay on sera derived from the same sample of blood and animals were placed accordingly into two groups, high (>1% binding at 1:500 dilution) and low responders (<1% binding at 1;500 dilution) and compared to the control group.

Figure 6:
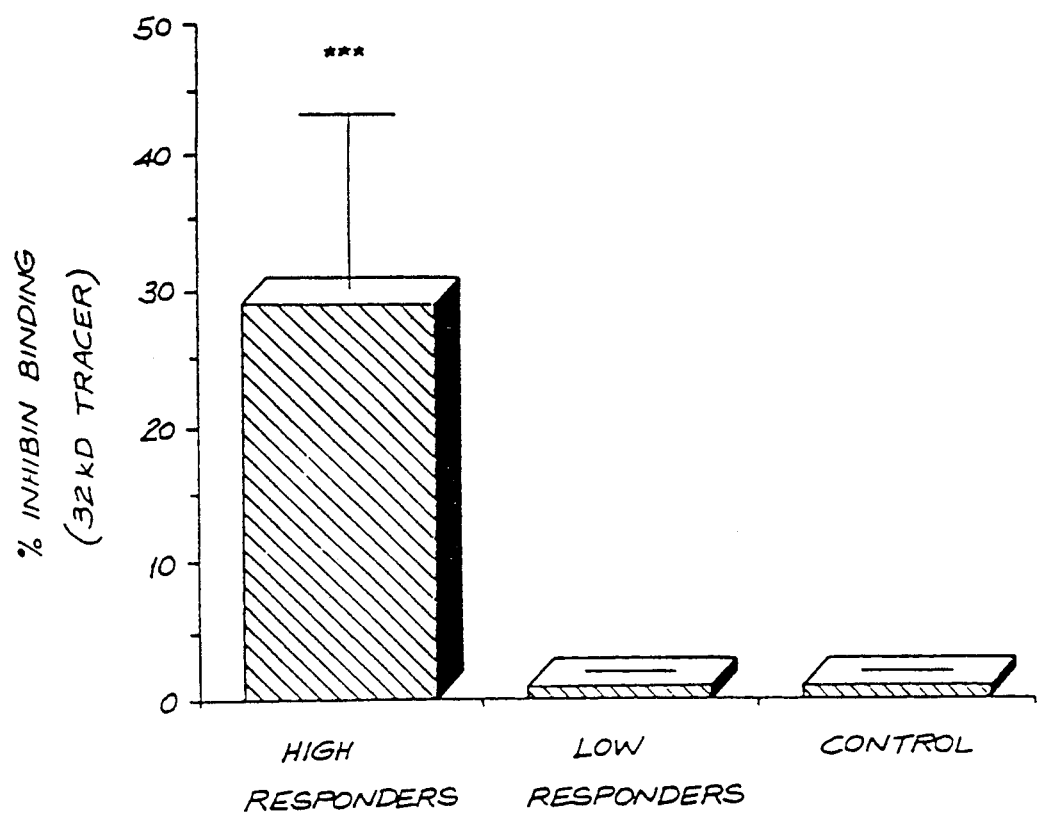
FIG. 6 shows the binding of sheep antibodies, as serum diluted 1:500, to iodinated 31 kD bovine inhibin. The sera are grouped as high responders (≧1% binding) and low responders (<1% binding) and controls (not vaccinated with active ingredient). The data show that there is a significant difference between the high responders and the other two groups (P<0.001; students t-test). Data are the mean±sem; number of animals per group is as shown in FIG. 7.
Figure 7:
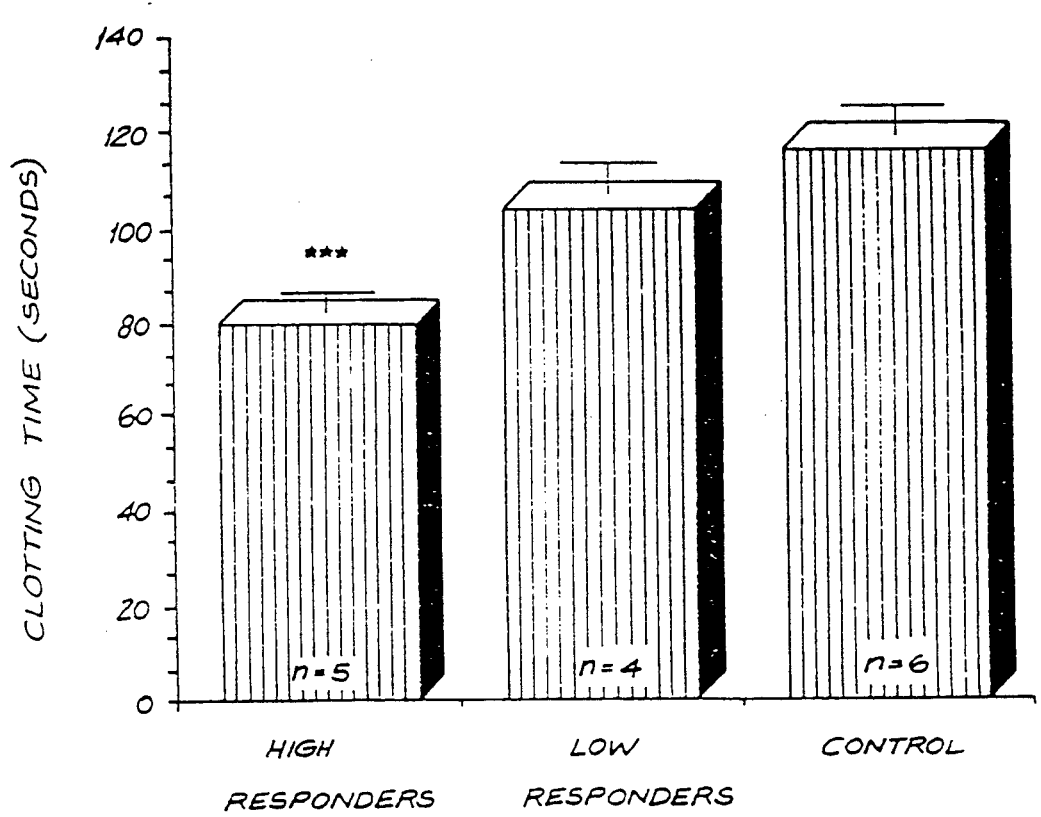
FIG. 7 shows the clotting time (in seconds) between the serum groups shown in FIG. 6. The data show that there is a significant difference between the high responders and the other two groups (P<0.001; students t-test). Data are the mean±sem; n=number of animals per group.

Immunisation of sheep against inhibin $\alpha$ subunit results in significantly elevated inhibin binding (FIG. 6) and faster clotting times (FIG. 7). The antibodies are operating as antagonists of inhibin activity and indicate that other chemicals that act as inhibin antagonists and/or other proteins such as activin and TGF-$\beta$ with effects known to be opposite to those of inhibin can be administered to achieve the same effect.

INDUSTRIAL APPLICATIONS

The methods of the invention are applicable to the treatment of blood clotting disorders using inhibin or inhibin antagonists or compositions incorporating inhibin or inhibin antagonists.

Delay of clotting or thrombic processes can be achieved by administration of inhibin whereas antagonists to inhibin can be utilised to enhance clotting processes.

These aspects of the invention find utility in the treatment of haemorrhaging and clotting disorders and in cardiovascular therapy in general.

Methods for treating immune dysfunction with inhibin and activin are also described as well as methods for promoting tissue growth using activin.

We claim:

1. A method for treating a host having autoimmune disease, comprising immunizing the host with a composition of matter comprising a substance selected from the group consisting of inhibin, and inhibin composition, the alpha subunit of inhibin, an alpha subunit composition, and combinations thereof, in an amount effective to treat the autoimmune disease.

2. A method for treating a host having autoimmune disease, comprising administering to the host a composition of matter comprising a substance selected from the group consisting of activin, an activin composition, an inhibin antagonist, an inhibin antagonist composition, and combinations thereof, in an amount effective to treat the autoimmune disease.

3. A method for suppressing transplant rejection in a host needing such suppression, comprising immunizing the host with a composition of matter comprising a substance selected from the group consisting of inhibin, an inhibin composition, the alpha subunit of inhibin, an alpha subunit composition, and compositions thereof, in an amount effective to suppress the transplant rejection.

4. A method for suppressing transplant rejection in a host needing such suppression, comprising administering to the host a composition of matter comprising a substance selected from the group consisting of activin, an activin composition, an inhibin antagonist, an inhibin antagonist composition, inhibin antibodies, an inhibin antibody composition, alpha subunit antibodies, an alpha subunit antibody composition, and combinations thereof, in an amount effective to suppress the transplant rejection.

5. A method for monitoring the immune status of a host, comprising administering to the host a substance selected from the group consisting of inhibin, an inhibin composition, activin, or an activin composition, and measuring the ability of the host's immune system to react to said substance.

6. A method for treating a host exhibiting an immunosuppressive state or having an autoimmune disease, comprising administering to the host a composition of matter comprising a substance selected from the group consisting of inhibin, an inhibin composition, and combinations thereof, in an amount effective to treat the immunosuppressive state or autoimmune disease.

7. A method for stimulating the immune response of a host, comprising administering to the host a composition of matter comprising a substance selected from the group consisting of inhibin, an inhibin composition, and combinations thereof, in an amount effective to stimulate the immune response of the host.

* * * * *

UNITED STATES PATENT AND TRADEMARK OFFICE
CERTIFICATE OF CORRECTION

PATENT NO. : 5,196,192

DATED : March 23, 1993

INVENTOR(S) : David M. DE KRETSER et al.

It is certified that error appears in the above-identified patent and that said Letters Patent is hereby corrected as shown below:

At column 19, line 24, (i.e., claim 3, line 6), change "compositions" to ---combinations---.

Signed and Sealed this

Twelfth Day of April, 1994

Attest:

BRUCE LEHMAN

Attesting Officer

Commissioner of Patents and Trademarks